United States Patent [19]

Kita et al.

[11] Patent Number: 4,623,734
[45] Date of Patent: Nov. 18, 1986

[54] METHOD FOR PRODUCTION OF MALEIMIDES

[75] Inventors: Yuichi Kita, Akashi; Kentaro Sakamoto, Hyogo; Masao Baba; Atsushi Okubo, both of Himeji, all of Japan

[73] Assignee: Nippon Shokubai Kagaku Kogyo Co., Ltd., Japan

[21] Appl. No.: 745,414

[22] Filed: Jun. 14, 1985

[30] Foreign Application Priority Data

Jun. 18, 1984 [JP] Japan ............................. 59-123747
Jul. 10, 1984 [JP] Japan ............................. 59-141309
Mar. 6, 1985 [JP] Japan ............................. 60-42798
Apr. 4, 1985 [JP] Japan ............................. 60-70071

[51] Int. Cl.$^4$ ..................................... C07D 207/448
[52] U.S. Cl. ............................................. 548/545
[58] Field of Search .................................. 548/545

[56] References Cited

U.S. PATENT DOCUMENTS

| 2,182,178 | 12/1939 | Pinkernelle | 548/545 |
| 2,444,536 | 7/1948 | Searle | 548/549 |
| 2,566,992 | 9/1951 | Morgan et al. | 548/545 |
| 2,643,258 | 6/1953 | Miller et al. | 548/545 |

FOREIGN PATENT DOCUMENTS

| 0068770 | 6/1978 | Japan | 548/545 |
| 1041027 | 11/1966 | United Kingdom . | |

Primary Examiner—Richard L. Raymond
Assistant Examiner—D. B. Springer
Attorney, Agent, or Firm—Omri M. Behr

[57] ABSTRACT

A method for the production of maleimides, which comprises subjecting maleinamic acids to ring-closure imidation in an organic solvent capable of forming an azeotrope with water in the presence of an acid catalyst at a temperature in the range of 120° to 250° C. while removing the formed water in the form of an azeotrope with said organic solvent and thereafter purifying the produced maleimides.

20 Claims, No Drawings

METHOD FOR PRODUCTION OF MALEIMIDES

BACKGROUND OF THE INVENTION

1. Field of the Invention

This invention relates to a method for the production of maleimides. More particularly, this invention relates to a method for production of maleimides by ring-closure imidation of maleinamic acids.

2. Description of the Prior Art

Maleimides are compounds useful as raw materials for synthetic resins, medicines, and agricultural chemicals. Researches after methods for their production have long been under way. The most popular method of them all effects the production of maleimides by the dehydration cyclization of maleinamic acids with a dehydrating agent such as acetic anhydride. One version of this method is disclosed in U.S. Pat. No. 2,444,536. This method effects the production of maleimides by causing maleic anhydride to react upon amines thereby forming maleinamic acids and dehydration cyclizing and, at the same time, imidating the maleinamic acids in the presence of acetic anhydride and sodium acetate. This method, however, has the disadvantage that the imidation requires expensive acetic anhydride to be used in at least an equivalent relative to the maleinamic acid and the separation and recovery of the formed maleimide from the imidation reaction solution necessitates use of a large volume of water and, as the result, entails disposal of a large amount of an acetic acid-containing effluent at great expense. Thus, this method may well be called a too expensive method for commercial production of maleimides.

A method which has no use for such a chemical dehydration agent as acetic anhydride is disclosed in British Pat. No. 1,041,027. This method effects the production of maleimides by thermally dehydrating and cyclizing maleinamic acids in conjunction with a solvent such as, for example, toluene, xylene, or chlorobenzene having a boiling point exceeding 80° C. and serving as a diluent and an acid catalyst such as sulfur trioxide, sulfuric acid, or ortho-phosphoric acid, and distilling the system thereby causing azeotropic expulsion of the consequently formed water in conjunction with the solvent. As compared with the method which uses acetic anhydride, this method proves advantageous in that it does not require use of a large amount of such an expensive dehydrating agent as acetic anhydride and further that the formed maleimides are separated and recovered with ease. This method nevertheless has the disadvantage that the yield of the imidation is low as compared with that obtainable by the method using acetic anhydride. This disadvantage is logically explained by a postulate that compared with the method which effects the imidation by the use of acetic anhydride, the method which effects the imidation by performing thermal dehydration in the specific solvent as described above involves a high reaction temperature and, therefore, tends to induce secondary reactions and inevitably manages to produce maleimides abounding with impurities and further that since maleimides are thermally unstable, the maleimides produced at all are degenerated during the course of the reaction.

There is another method which, as disclosed in Japanese Patent Laid-open No. SHO 53(1978)-68,700 and Japanese Patent Publication No. SHO 57(1982)-42,043, comprises causing maleic anhydride to react on amines in the presence of an organic solvent thereby forming maleinamic acids and subjecting the maleinamic acids as held in a state not isolated from the reaction system to dehydration and cyclization in the presence of such an aprotic polar solvent as dimethyl formamide or dimethyl sulfoxide and an acid catalyst. By this method, there is offered recognizable improvement in yield as compared with the second method described above. This method, however, has these disadvantages, that the cost of production of maleimides is high because expensive and highly toxic aprotic polar solvent such as dimethyl formamide is used in a large amount, that the solvent such as dimethyl formamide is degenerated by the action of an acid catalyst used in the reaction and, therefore, the solvent is lost greatly, and that since the aprotic polar solvent used in the reaction has a high boiling point, the solvent is removed from the produced maleimides with great difficulty.

Yet another method has been proposed (as in Japanee Patent Laid-open No. SHO 47(1972)-27,974) which effects the imidation of maleinamic acids by directly heating the acids in the presence of an acid catalyst. Unfortunately, this method is not free from the following disadvantages that a large amount of resinous impurities is produced in the reaction vessel resulting to obtain maleimides in low yield, and that, moreover, the crude maleimides inevitably contain by-produced maleic acid in great deal.

In addition to the disadvantages described above, these methods for the production of maleimides are invariably attended by the essential requirement that since by-products occur in not negligible amounts during the course of imidation, the produced maleimides should be purified in order to acquire high purity at great expenses.

As means of purification such impure maleimides, there have been proposed a method which comprises pouring the reaction solution into a large amount of cold water thereby inducing precipitation of crystals, separating the crystals by filtration, washing the crystals with a large amount of water or washing them with a dilute aqueous solution of sodium carbonate or aqueous solution of sodium hydroxide, and thereafter drying the washed crystals (U.S. Pat. No. 2,444,536 and Japanese Patent Laid-open No. SHO 55(1980)-149,253) and a method which comprises neutralizing the reaction solution containing a maleimide in an organic solvent with a dilute aqueous solution of a weak alkali and washing the neutralized reaction solution with water thereby separating the organic solvent therefrom (Japanese Patent Laid-open No. SHO 53(1978)-68,770).

In accordance with these methods, however, it is difficult to obtain maleimides of high purity because the by-products which occur during the course of imidation are as insoluble in water as resinous substances and maleimides. Since these methods involve use of large amounts of water, they inevitably entail the problem of safe disposal of large amounts of washings. They are deficient in practical utility and prove disadvantageous from the economic point of view.

An object of this invention, therefore, is to provide a novel method for the production of maleimides.

Another object of this invention is to provide a method for inexpensively producing maleimides in high yields by the ring-closure imidation of corresponding maleinamic acids effected by a safe and simple procedure.

Still another object of this invention is to provide a method for the production of maleimides of high purity.

SUMMARY OF THE INVENTION

The objects described above are attained by the present invention providing a method for the production of maleimides, which comprises subjecting maleinamic acids to ring-closure imidation in an organic solvent capable of forming an azeotrope with water in the presence of an acid catalyst at a temperature in the range of 120° to 250° C. while removing the formed water in the form of an azeotrope with the organic solvent and thereafter purifying the produced maleimides.

The reaction mentioned above is additionally carried out by effecting the ring-closure imidation in the presence of a compound of at least one metal selected from the group consisting of zinc, chromium, cobalt, nickel, iron, aluminum, and palladium and a stabilizer.

The purification of the produced maleimides are carried out by adding to the crude maleimides organic acid or inorganic acid in an amount of at least 1% by weight based on the maleinamic acids used as the raw material, treating the resultant mixture at a temperature in the range of 5° to 100° C., and washing the resultant organic layer with water thereby depriving the organic layer of water-soluble impurities.

Alternatively, the purification of the crude maleimides are effected by washing the crude maleimides with water and distilling the washed maleimides in the presence of a stabilizer.

DESCRIPTION OF PREFERRED EMBODIMENTS

The method for the production of maleimides according to this invention comprises subjecting maleinamic acids to ring-closure imidation in an organic solvent capable of forming an azeotrope with water in the presence of an acid catalyst at a temperature in the range of 120° to 250° C. while removing the formed water in the form of an azeotrope with the organic solvent and therefter purifying the produced maleimides.

The maleinamic acids to be used in this invention are easily obtained generally by the reaction of primary amines with maleic anhydride. They are desired to be compounds represented by the following general formula I.

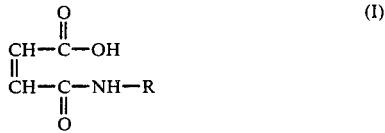

(I)

wherein R denotes a member selected from the class consisting of alkyl of 1 to 20 carbon atoms, phenyl, benzyl, cyclohexyl, pyridyl, and quinolyl groups, and the same groups as mentioned above and possessed of halogen, carboxyl, or nitro substituents; providing that said alkyl groups or phenyl groups are more desirable than the other groups mentioned.

Examples of the primary amine particularly useful as the raw material for the maleinamic acid in this invention include methylamine, ethylamine, n-propylamine, isopropylamine, n-butylamine, sec-butylamine, isobutylamine, tert-butylamine, n-hexylamine, n-dodecylamine, allylamine, benzylamine, cyclohexylamine, aniline, nitroaniline, aminophenol, aminobenzoic acid, anisidine, ethoxyphenylamine, monochloroaniline, dichloroaniline, toluidines, xylidines, and ethylanilines.

Synthesis of a maleinamic acid proceeds virtually stoichiometrically. For example, the maleinamic acid can be synthesized by causing the amine in an amount of 0.8 to 1.5 mols, preferably 0.9 to 1.2 mols, to react upon each mol of maleic anhydride. If the amount of the amine relative to that of the maleic anhydride exceeds the upper limit of the aforementioned range, the amount of an acid catalyst to be required when the product of this reaction is directly used in the subsequent imidation must be increased in a large excess and the amounts of the products of secondary reactions attendant on the imidation are increased possibly to the extent of lowering the yield of the imidation. Thus, the range mentioned above must be observed to ensure satisfactory results of the imidation.

The organic solvent capable of forming an azeotrope with water and usable for the purpose of this invention is desired to be a solvent which permits the water formed in the dehydration cyclization to be removed by azeotropic distillation and refrains from participating in the reaction. Concrete examples which meet this description include benzene, toluene, xylenes, ethylbenzene, isopropylbenzene, cumene, mesitylene, tert-butylbenzene, pseudocumene, trimethylhexane, octane, tetrachloroethane, nonane, chlorobenzene, ethyl cyclohexane, petroleum fractions boiling at 120° to 170° C., m-dichlorobenzene, secbutylbenzene, p-dichlorobenzene, decane, p-cymene, o-dichlorobenzene, butylbenzene, decahydronaphthalene, tetrahydronaphthalene, dodecane, naphthalene, cyclohexylbenzene, and petroleum fractions boiling at 170° to 250° C. For the purpose of enabling the reaction to proceed smoothly and satisfying the economic conditions of the production, the amount of this solvent to be used in the reaction is desired to fall in the range of 1 to 20 times, preferably 3 to 7 times (by weight) the amount of the maleinamic acids.

Examples of the acid catalyst effectively used herein include sulfuric acid, sulfuric anhydride, p-toluenesulfonic acid, ortho-phosphoric acid, meta-phosphoric acid, and pyrophosphoric acid. The amount of the acid catalyst is desired to fall in the range of 2 to 8 mol%, preferably 10 to 30 mol%, based on the maleinamic acids.

In the reaction described above, a metal-containing compound is desired to be used additionally as a promoter. The metal-containing compound is a compound of at least one metal selected from the group consisting of zinc, chromium, palladium, cobalt, nickel, iron, and aluminum. Compounds of zinc are desirable selection. Thus, the metal-containing compound is specifically selected from among oxides, acetates, maleates, succinates, nitrates, phosphates, chlorides, bromides, iodides, and sulfates of the aforementioned metals. Preferable compounds are acetic acid salts of these metals and zinc acetate is the most preferable. The amount of the metal-containing compound to be used is desired to fall in the range of 0.005 to 0.5 mol, preferably 0.01 to 0.1 mol as metal per 100 mols of the maleinamic acids.

The aforementioned reaction produces even better results when it is allowed to proceed in the presence of a stabilizer. Examples of the stabilizer effectively usable herein include quinones such as methoxybenzoquinone, hydroquinone, and tert-butyl hydroquinone; phenols such as p-methoxyphenol, tert-butyl catechol, alkyl phenols, and alkyl bisphenols; thiodipropionic esters such as dilauryl thiodipropionate; dithiocarbamates such as zinc dimethyl dithiocarbamate and copper dibutyl dithiocarbamate; salycylates; alkylated diphenylamines; phenothiiazines such as phenothiazine and methylene blue; mercaptoimidazoles such as 2-mercaptobenzimidazole; and triphenyl phosphates. This stabilizer plays the part of enabling the maleimides formed by the imidation to remain intact even at the elevated temperatures prevailing during the course of the imidation. If the amount of the stabilizer to be used is very small, the added stabilizer is not so effective as expected. If the amount is excessive, there ensues the problem that the added stabilizer mingles into the product of the reaction. Thus, the amount of the stabilizer so used is desired to fall in the range of 0.005 to 0.5 mol, preferably 0.05 to 0.3 mol, per 100 mols of the maleinamc acids.

The first step in the practice of the method of this invention is to add an amine to a solution of maleic anhydride in an organic solvent and heat the resultant mixture at a temperature not exceeding 150° C., preferably falling in the range of 30° to 120° C. for a period of 15 to 120 minutes, preferably 30 to 60 minutes, so as to effect reaction of the maleic anhydride with the amine and give rise to a corresponding maleinamic acids. The next step is to heat the maleinamic acids in a state not isolated from the resultant reaction solution, with the aforementioned acid catalyst and optionally the metal-containing compound and the stabilizer added thereto, at a temperature in the range of 120° to 250° C., desirably 140° to 220° C. for a period of 1 to 15 hours, desirably 2 to 7 hours and continue the ensuing reaction while removing the formed water from the system by azeotropic distillation. As the result, corresponding maleimides are obtained in a high yield. Particularly when the reaction temperature is kept in the range of 180° to 250° C., since accelerating the reaction velocity the selectivity of the maleimides is notably improved without requiring the combined use of the metal-containing compound and the stabilizer. The effect of the use of the temperature in the specific range is conspicuous when the maleimides to be produced is of a type possessing an aromatic type substituent, and alicyclic type substituent, or an aliphatic type substituent. The solvent to be used in the reaction is selected in due consideration of the ability to dissolve the produced maleimides, the price, the ease of handling, and the possession of a boiling point meeting the reaction conditions. Under certain reaction conditions, the solvent may be advantageously used under increased pressure. The stabilizer can also be selected in due consideration of the reaction conditions and the kind of the maleimides to be produced.

The maleimide which is consequently obtained is a compound represented by the general formula II, for example.

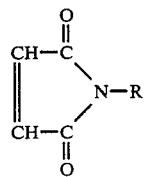

(II)

wherein R has the same meaning as defined above. Typical examples of the maleimides include N-methyl maleimide, N-ethyl maleimide, N-n-propyl maleimide, N-isopropyl maleimide, N-n-butyl maleimide, N-sec-butyl maleimide, N-tert-butyl maleimide, N-n-hexyl maleimide, N-n-dodecyl maleimide, N-allyl maleimide, N-benzyl maleimide, N-cyclohexyl, maleimide, N-phenyl maleimide, N-nitrophenyl maleimide, N-hydroxyphenyl maleimide, N-methoxyphenyl maleimide, N-ethoxyphenyl maleimide, N-monochlorophenyl maleimide, N-dichlorophenyl maleimide, N-monomethylphenyl maleimide, N-dimethylphenyl maleimide, and N-ethylphenyl maleimide. Of course, the maleimides which this invention is intended to embrace are not limited to the examples cited above.

The crude maleimides which are produced in consequence of the imidation described above is purified by the following procedure, for example. The purification of the crude maleimides are accomplished by adding to the crude maleimides an organic acid or inorganic acid in an amount of at least 1% by weight based on the maleinamic acids used as the raw material, treating the resultant mixture at a temperature in the range of 5° to 100° C. and then washing the resultant organic layer with water thereby depriving it of water-soluble impurities.

For the acid used in this acid treatment to be fully effective as expected, the distinction between the organicity and inorganicity of the acid is irrelevant. Typical examples of the acid advantageously usable herein include ortho-phosphoric acid, pyrophosphoric acid, sulfuric acid, sulfuric anhydride, fuming sulfuric acid, methane sulfonic acid, chlorosulfonic acid, chloromaleic acid, paratoluenesulfonic acid, and trifluoroacetic acid. Among other acids, sulfonic acids, sulfuric acid, sulfuric anhydride, and fuming sulfuric acid are desirable selections. One member or a mixture of two or more members selected from among the acids enumerated above can be used effectively in this invention.

The amount of the acid to be used herein is a matter to be suitably decided in due consideration of the amount of impurities in the crude maleimides, the purity of the product to be obtained, the yield of the purification, the efficiency of work, and the economy of the production. This amount is not critical to the successful practice of the method of this invention. When any ordinary crude maleimides are purified in accordance with this invention, the effect of the acid treatment is obtained so long as the amount of the acid so used is at least 1% by weight based on the maleinamic acids used as the raw material. The upper limit of this amount can be fixed substantially at a freely selected value. Where the yield of purification, the efficiency of work, the economy of prorduction, and so on are taken into consideration, this amount may be fixed at any level not exceeding 30% by weight. Preferably this amount falls in the rang of 5 to 10% by weight.

The acid treatment is carried out at a temperature in the range of 5° to 100° C., preferably 20° to 70° C., and in the time of 5 to 120 minutes, preferably 10 to 60 minutes. If this treatment is carried out at a temperature exceeding 100° C., the yield is substantially decreased because secondary treatments occur so heavily to require a special treatment for their removal and the produced maleimides undergoes polymerization. If this treatment is carried out at a temperature lower than 5° C., the purity of the produced maleimides and the yield of production are not sufficient because the effect of the treatment is not ample and the maleimies produced in the reaction solution is precipitated and removed in conjunction with by-products.

Even when sulfuric acid is used as an acid catalyst in the imidation, the acid treatment requires new addition of sulfuric acid in the amount defined above. The acid catalyst to be used in the imidation is in an amount falling within the range of 10 to 30 mol% based on the maleinamic acids used as the raw material. If, at this time, the amount of the sulfuric acid put to use in the imidation has been increased with the amount of sulfuric acid estimatedd to be used in the subsequent step of acid treatment, the purification proves disadvantageous from the commercial point of view because the yield of the production of the maleimides are notably low. This acid treatment is not sufficiently effective when it is carried out after the reaction mixture resulting from the imidation has been washed with water or when the organic layer obtained by separating the acid catalyst layer from the reaction mixture has been washed with water.

By carrying out the acid treatment specified by this invention as described above, the by-products formed during the course of the ring-closure imidation and contained consequently in the reaction mixture is enabled to be precipitated substantially in its entire amount in the form of a viscous resinous substance from the reaction mixture. This precipitate can be easily separated from the reaction mixture by an ordinary means such as filtration or decantation. Consequently, there is obtained an organic layer containing the produced maleimides substantially exclusively. Even when the acid treatment is carried out directly on the reaction mixture in a state not deprived of the acid catalyst used in the ring-closure imidation, the treatment is as effective as when it is carried out after the reaction mixture has been deprived of the acid catalyst.

When the organic layer obtained in consequence of the acid treatment is washed in water of an amount 1 to 5 times (by weight) the amount of the maleinamic acids used as the raw material at a temperature in the range of 10° to 50° C., the unaltered acid and the by-products remaining in minute amounts in the organic layer are removed. The water to be used in this washing treatment may be pure water, service water, or city water. Otherwise, weakly alkaline water or weakly acidic water may be used. This washing treatment is required to lower the acid content in the organic layer below 0.5% by weight, preferably below 0.1% by weight. Thereafter, the maleimides containing substantially no impurity can be safely obtained by expelling the organic solvent from the organic layer by distillation.

By the washing treatment performed in the present step, the impurities still remaining in minute amounts in spite of the acid treatment are removed and the unaltered acid is removed at the same time. During the course of the separation by vaporization of the organic solvent from the reaction solution resulting from the acid treatment, if part of the acid is suffered to remain in the reaction solution, it induces the produced maleimide to undergo polymerization and brings about a decrease in the purity of the maleimides. It is suspected that the heat evolved by the polymerization will cause troubles and possibly jeopardize the safety of the operation involved.

The crude maleimides can be purified otherwise by the following procedure, for example. The purification of the crude maleimides are attained by washing with water the crude maleimides resulting from the ring-closure imidation of the maleinamic acids and then distilling the washed crude maleimides in the presence of a stabilizer.

Concerning the work of purifying the crude maleimides by distillation, the inventors studied various distillation conditions with a view to developing a solution capable of overcoming the high susceptibility to polymerization which the maleimides inevitably manifests owing to its peculiar molecular structure. They have consequently found that the unaltered or by-produced maleic acid, the unaltered maleinamic acids, the acid used as the catalyst, and the acid component such as acetic anhydride or acetic acid used as the dehydrating agent which are contained as impurities in the crude maleimides, go to promote the polymerization of the maleimides during the distillation. Particularly when the acid component is suffered to remain in the crude maleimides in a concentration exceeding 1% by weight, a level variable more or less with the kind of the N-substituent of the maleimides, this acid component remarkably promotes the polymerization and, at times, even go the length of causing the maleimide to be polymerized virtually wholly during the distillation.

The inventors, based on the discovery described above, continued a study in search of a method for removal of the mischievous acid component. They have consequently found that this removal of the acid component is easily attained by washing the crude maleimides with water and that the crude maleimides resulting from the washing treatment is refined to high purity in a high yield during the distillation because it is effectively prevented from the otherwise possible polymerization due to the heat of the distillation. The washing treatment mentioned above sufficiently fulfils its purpose by lowering the concentration of the acid component in the crude maleimides generally below 0.5% by weight, a level variable with the kind of the N-substituent of the maleimides. Preferably, the concentration is lowered by this treatment below 0.1% by weight. The manner of the washing can be freely selected in due consideration of the condition of the mixture which has just resulted from the reaction. Where the crude maleimides are obtained in a solid state at the end of the reaction, for example, the removal of the acid component is efficiently effected by first reducing the crude maleimides to a powdered form and then washing the powdered crude maleimides with water. Where the reaction has involved use of an organic solvent, the removal of the acid component is accomplished by giving the washing treatment to the reaction solution after completion of the reaction. The water to be used for this washing treatment is not limited to pure water, service water, and city water. It may be weakly alkaline or weakly acidic water.

The crude maleimides which have undergone the washing treatment are then mixed with a stabilizer and distilled. Examples of the stabilizer effectively usable herein include phenols such as methoxybenzoquinone, hydroquinone, tert-butyl hydroquinone; phenols such as p-methoxyphenol, tert-butyl catechol, alkyl phenols, and alkyl bisphenols; thiodipropionic esters such as dilauryl thiopropionate; dithiocarbamates such as zinc dimethyl dithiocarbamate and copper dibutyl dithiocarbamate; salycylates; alkylated diphenylamines; phenothiazines such as phenothiazine and methylene blue; mercaptoimidazoles such as 2-mercaptobenzimidazole; and triphenyl phosphates. From the group indicated above, a suitable stabilizer is selected by taking into due consideration the kind of the maleimides under treatment and the requirement that the stabilizer should avoid mingling into the extract under the distillation conditions adopted.

According to the results of the inventors' study, the stabilizer selected from among copper dimethylthiocarbamate, zinc dimethyldithiocarbamate, copper dibutyldithocarbamate, and copper salicylate, particularly copper dibutyldithiocarbamate, remains in the bottoms and defies expulsion during the course of the distillation and manifests a conspicuous effect in preventing the maleimide from undergoing polymerization.

The amount of the stabilizer to be added to the maleimides under treatment are not specifically defined. The stabilizer is used in an amount generally exceeding 10 ppm (by weight) and desirably falling in the range of 100 to 2000 ppm (by weight), preferably 500 to 1000 ppm (by weight).

The conditions of the distillation are freely selected on the basis of the relation between the temperature and vapor pressure of the maleimide. Since the susceptibility of the maleimides to polymerization grows with the heightening temperature, it is advantageous to carry out the distillation at as low a temperature as permissible.

Now, the present invention, will be described more specifically below with reference to working examples. It is to be understood naturally that the present invention is not limited to these working examples.

EXAMPLE 1

A glass flask having an inner volume of 1 liter was fitted with a thermometer, a stirrer, and a water separator. Then, a solution of 53 g of powdered maleic anhydride in 50 g of tetrahydronaphthalene was placed in the glass flask. To the glass flask whose interior temperature was adjusted in advance to 90° C., a solution of 50 g of aniline in 400 g of tetrahydronaphthalene was added gradually and piecemeal over a period of 30 minutes to synthesize a tetrahydronaphthalene slurry of N-phenyl maleinamic acid. The yield of N-phenyl maleinamic acid based on aniline was 99.4 mol%.

The slurry containing the N-phenyl maleinamic acid and 10 g of ortho-phosphoric acid added thereto were heated at 210° C. for three hours. The resultant reaction mixture was cooled to 30° C., washed with water, and distilled under a vacuum to expel tetrahydronaphthalene and obtain 78 g of N-phenyl maleimide crystals. By liquid chromatography, the crystals were found to have purity of 87.3% by weight, indicating the yield thereof to be 73.2 mol%.

EXAMPLE 2

A glass flask having an inner volume of 3 liters was fitted with a thermometer, a stirrer, and a water separator. In this reactor, 240 g of a solution containing 120 g of maleic anhydride in xylene was placed. Then, a solution containing 220 g of dodecylamine in 1880 g of xylene was added gradually and piecemeal over a period of 120 minutes at 40° C. to the reactor. After the addition was completed, the mixture in the reactor and 65.4 g of orthophosphoric acid (purity 89% by weight) added thereto were heated at 215° C. for 1 hour under 4.4 kg/cm²G. to effect reaction. The resultant reaction mixture was cooled to 30° C., washed with 400 ml of water, and separated into a water layer and a xylene layer. The xylene layer was separated by filtration to effect removal of insolubles. The xylene layer was distilled to expel xylene. Consequently, there was obtained 258 g of slightly impure N-dodecyl maleimide. This product was found to have purity of 85.3% by weight, indicating the yield to be 69.9 mol% based on dodecylamine.

EXAMPLE 3

A vertical reaction tank measuring 600 cm in inside diameter and 800 cm in height and fitted with a thermometer, a heating jacket, a stirrer and a water separator was charged with a mixed solution comprising 15 kg of maleic anhydride and 30 kg of xylene and heated to an internal temperature of 70° C. Then, to the reaction tank, a mixed solution containing 13.5 kg of aniline and 70 kg of xylene was added gradually and piecemeal over a period of 100 minutes. Consequently, there was obtained a slurry solution containing white crystals of N-phenyl maleimide.

Subsequently, 3.2 kg of ortho-phosphoric acid (purity 89% by weight), 9.6 g of zinc acetate, and 26.7 g of p-methoxyphenol were added.

Then, the internal temperature of the reaction tank was elevated to 136° C. and kept at this level for six hours by means of the heating jacket to promote the ensuing reaction. The water formed in the meantime was distilled in conjunction with xylene. The total amount of water thus expelled was 2.5 liters.

Then, the resultant reaction mixture was cooled to 30° C. and mixed with 30 liters of water added thereto for one hour. After the stirring, the reaction mixture was left standing for 30 minutes to be separated into a xylene layer and a water layer. Then the water layer was separated. The procedure was repeated once more. The xylene layer so washed with water was distilled under a vacuum to expel xylene. Consequently, there were obtained 23 kg of N-phenyl maleimide crystals. By liquid chromatography, the crystals were found to have purity of 93.6% by weight.

Thus, the yield of the crystals is calculated to be 85.7 mol% based on aniline as the raw material.

EXAMPLE 4

The procedure of Example 3 was repeated, except that butylbenzene was used in the place of xylene as the solvent, phenothiazine was used in the place of p-methoxyphenol, and the reaction temperature was changed from 136° C. to 185° C. Consequently, there were obtained 24.7 kg of N-phenyl maleimide crystals. By liquid chromatography, the crystals were found to have purity of 90.8% by weight.

Thus, the yield of the crystals is calculated to be 89.3 mol% based on aniline used as the raw material.

EXAMPLES 5-21 AND CONTROL 1

A glass flask having an inner volume of 1 liter was fitted with a thermometer, a stirrer, and a water separator. Then, a solution of 53 g of powdered maleic anhydride in 50 g of xylene was added to the aforementioned glass flask. To the glass flask whose internal temperature was adjusted in advance to 130° C., a solution of 50 g of aniline in 400 g of xylene was added gradually and piecemeal over a period of 30 minutes to synthesize a slurry xylene solution of N-phenyl maleinamic acid. The yield of the N-phenyl maleinamic acid was found to be 99.2 mol% based on aniline.

The slurry solution so obtained and a varying acid catalyst, a varying metal-containing compound, and a varying stabilizer added therein in varying amounts based on the N-phenyl maleinamic acid contained in the slurry solution as indicated in Table 1 were heated at 140° C. for three hours to effect reaction. The reaction mixture consequently formed was cooled to 30° C., washed with water, and distilled under a vacuum to expel xylene. Consequently, there were obtained N-phenyl maleimide crystals. The crystals were tested by liquid chromatography for purity. The results are shown in Table 1.

filtrate was distilled to expel cyclohexane. Consequently, there were obtained 82 g of bright yellow crystals of N-phenyl maleimide. The purity of the crystals was found to be 99.4% by weight, indicating the yield thereof to be 87.6 mol% based on the N-phenyl maleinamic acid.

CONTROL 2

TABLE 1

|  | Acid catalyst (mol %) | | Metal containing compound (mol % as metal) | | Stabilizer (mol %) | | Amount produced (g) | Purity (% by wt.) | Yield (mol %) (based on maleinamic acid) |
| --- | --- | --- | --- | --- | --- | --- | --- | --- | --- |
| Control 1 | Ortho-phosphoric acid | 20 | Zinc Acetate | 0 | | 0 | 82 | 74.8 | 65.9 |
| Example 5 | Ortho-phosphoric acid | 20 | Zinc Acetate | 0.03 | | 0 | 86 | 84.7 | 78.3 |
| Example 6 | Ortho-phosphoric acid | 20 | Zinc Acetate | 0.01 | p-methoxy-phenol | 0.1 | 83 | 82.4 | 73.5 |
| Example 7 | Ortho-phosphoric acid | 20 | Zinc Acetate | 0.03 | p-methoxy-phenol | 0.1 | 85 | 93.1 | 85.1 |
| Example 8 | Ortho-phosphoric acid | 20 | Palladium nitrate | 0.03 | p-methoxy-phenol | 0.1 | 85 | 86.2 | 78.8 |
| Example 9 | Ortho-phosphoric acid | 20 | Aluminum oxide | 0.03 | p-methoxy-phenol | 0.1 | 83 | 78.7 | 70.2 |
| Example 10 | Ortho-phosphoric acid | 20 | Chromium oxide (III) | 0.03 | p-methoxy-phenol | 0.1 | 86 | 87.2 | 80.6 |
| Example 11 | Ortho-phosphoric acid | 20 | Zinc oxide | 0.03 | p-methoxy-phenol | 0.1 | 84 | 91.2 | 82.4 |
| Example 12 | Ortho-phosphoric acid | 20 | Cobalt phosphate | 0.03 | p-methoxy-phenol | 0.1 | 82 | 78.5 | 69.2 |
| Example 13 | Ortho-phosphoric acid | 20 | Nickel sulfate | 0.03 | p-methoxy-phenol | 0.1 | 83 | 79.0 | 70.5 |
| Example 14 | Ortho-phosphoric acid | 20 | Iron oxide(II) | 0.03 | p-methoxy-phenol | 0.1 | 81 | 82.3 | 71.7 |
| Example 15 | Sulfuric acid | 20 | Zinc acetate | 0.03 | p-methoxy-phenol | 0.1 | 68 | 92.1 | 67.3 |
| Example 16 | P-toluenesulfonic acid | 20 | Zinc acetate | 0.03 | p-methoxy-phenol | 0.1 | 80 | 89.6 | 77.1 |
| Example 17 | Ortho-phosphoric acid | 20 | Zinc acetate | 0.03 | Phenothiazine | 0.1 | 84 | 92.2 | 83.3 |
| Example 18 | Ortho-phosphoric acid | 20 | Zinc acetate | 0.03 | Hydroquinone | 0.1 | 82 | 91.3 | 80.5 |
| Example 19 | Ortho-phosphoric acid | 20 | Zinc acetate | 0.005 | p-methoxy-phenol | 0.1 | 83 | 81.4 | 72.6 |
| Example 20 | Ortho-phosphoric acid | 20 | Zinc acetate | 0.05 | p-methoxy-phenol | 0.1 | 84 | 90.9 | 82.1 |
| Example 21 | Ortho-phosphoric acid | 20 | Zinc acetate | 0.03 | p-methoxy-phenol | 0.01 | 83 | 90.1 | 80.4 |

EXAMPLES 22-25

The procedure of Example 7 was repeated, except that the kind of solvent and the temperature were varied as indicated below. The results are shown in Table 2.

TABLE 2

| Example | Solvent | Temperature (°C.) | Amount produced (g) | Purity (% by wt.) | Yield (mol %) |
| --- | --- | --- | --- | --- | --- |
| 22 | P-cymene | 180 | 90.5 | 91.5 | 89.0 |
| 23 | Mesitylene | 170 | 88.0 | 93.4 | 88.4 |
| 24 | Tetrahydro-naphthalene | 210 | 83.8 | 94.4 | 85.1 |
| 25 | Dodecane | 220 | 88.1 | 85.1 | 80.6 |

EXAMPLE 26

The procedure of Example 7 was followed, except that the temperature for the imidation was increased to 148° C. Consequently, there were obtained 91 g of yellow crystals.

Then, the crystals and 1700 ml of cyclohexane added thereto were heated at 75° C. for one hour to extract N-phenyl maleimide. The extract was filtered. The filtrate was distilled to expel cyclohexane. Consequently, there were obtained 82 g of bright yellow crystals of N-phenyl maleimide. The purity of the crystals was found to be 99.4% by weight, indicating the yield thereof to be 87.6 mol% based on the N-phenyl maleinamic acid.

When the procedure of Example 7 was repeated, except that the addition of the stabilizer and the metal-containing compound was omitted, heavy decomposition was observed to occur during the course of the reaction. The amount of water formed in consequence of the reaction was 16 ml. This value represents an excess of 65 mol% over the theoretical value of the amount of water to be formed by the imidation. The excess water is believed to have been formed by some secondary reaction. Further in the xylene solution, a brown fluffy substance appearing to be a polymer formed heavily. When this xylene solution was washed with water and distilled to expel xylene, there was obtained 80 g of a brown mass of N-phenyl maleimide. This mass was found to have purity of 70.3% by weight, indicating the yield thereof to be 60.5 mol% based on the N-phenyl maleinamic acid.

EXAMPLE 27

The same reactor as used in Example 7 was adopted. This reactor was charged with a solution 53 g of maleic anhydride in 200 g of chlorobenzene. Then, methylamine gas was blown in gradually and piecemeal at 30°

C. at a rate of 4.3×10$^{-3}$ mol/min. over a period of two hours to produce a white slurry of N-methyl maleinamic acid. Subsequently, the slurry and 22.5 g of ortho-phosphoric acid (purity 89% by weight), 0.1 g of phenothiazine, and 0.02 g of zinc acetate added thereto were heated at 134° C. for two hours to effect reaction. Thereafter, the resultant reaction mixture was cooled to 40° C., filtered, and distilled under a vacuum to expel chlorobenzene. Consequently, there was obtained 45 g of light yellow N-methyl maleimide having purity of 92.1% by weight. The yield of the product is calculated to be 72.5 mol% based on methylamine as the raw material.

By further distilling the impure N-methyl maleimide under vacuum of 35 mmHg (abs) at 128° C., there were obtained 38.5 g of white N-methyl maleimide crystals. The crystals were found to have purity of 99.6% by weight, indicating the yield thereof to be 67.1 mol% based on methylamine as the raw material.

EXAMPLE 28

A glass flask having an inner volume of 3 liters was fitted with a theremometer, a stirrer and a water separater. This reactor was charged with 240 g of a xylene solution containing 120 g of maleic anhydride. Then, a solution of 220 g of dodecylamine in 1880 g of xylene was added thereto gradually and piecemeal at 40° C. over a period of 120 minutes. After the addition was completed, the resultant mixture and 65.4 g of ortho-phosphoric acid (purity 89% by weight), 0.672 g of p-methoxyphenol and 0.05 g of zinc acetate added thereto were heated at 150° C. for four hours to effect reaction. Thereafter, the resultant reaction mixture was cooled to 30° C., washed with 400 ml of water, and separated into a water layer and a xylene layer. The xylene layer was filtered to effect removal of insolubles. The xylene layer now free from insolubles was distilled to expel xylene. Consequently there was obtained 260 g of slightly impure N-dodecyl maleimide. It was found to have purity of 91.2% by weight, indicating the yield thereof to be 75.3 mol% based on dodecylamine.

This impure N-dodecyl maleimide was distilled under a vacuum of 5 mmHg (abs) at 180° C. Consequentley, there was obtained 207 g of white N-dodecyl maleimide crystals. The crystals were found to have purity of 99.0% by weight, indicating the yield thereof to be 65.1 mol% based on dodecylamine as the raw material.

EXAMPLE 29

The same reactor as used in Example 7 was adopted. In this reactor, a solution of 120 g of maleic anhydride in 360 g of tetrahydronaphthalene was placed. Then, a solution of 220 g of dodecylamine and 1760 g of tetrahydronaphthalene was added thereto at 40° C. over a period of 120 minutes. After the addition was completed, the resultant mixture and 65.4 g of ortho-phosphoric acid (purity 89% by weight), 1.344 g of methoxybenzoquinone, and 0.1 g of zinc acetate added thereto were heated at 210° C. for one hour to effect reaction. Thereafter, the resultant reaction mixture was cooled to 30° C. and separated into a water layer and a tetrahydronaphthalene layer. The tetrahydronaphthalene layer was distilled to expel tetrahydronaphthalene. Consequently, there was obtained 285 g of slightly impure N-dodecyl maleimide. It was found to have purity of 92.3% by weight, indicating the yield thereof to be 83.5 mol% based on dodecylamine.

EXAMPLE 30

A flask provided with a thermometer, a condenser incorporating a moisture separator, a dropping funnel, and a stirrer was charged with 100 g of a petroleum fraction containing not less than 98% of an aromatic hydrocarbon having boiling points of 180° to 220° C. The petroleum fraction and 100 g of maleic anhydride added thereto were heated by elevating the internal temperature of the flask to 70° C. to dissolve the maleic anhydride in the petroleum fraction.

Then, a solvent of 90 g of aniline in 630 g of the same solvent as described above was added dropwise while under stirring over a period of 30 minutes to synthesize a slurry solution of N-phenyl maleinamic acid in the aforementioned solvent. During the course of this synthesis, the liquid temperature in the flask was kept cooled to 70° C. to repress otherwise possible evolution of heat.

Then, the aforementioned slurry solution and 20 g of ortho-phosphoric acid (85 weight% aqueous solution) added thereto were heated and stirred at 210° C. and left reacting for three hours, with the water formed by the reaction removed from the reaction system by azeotropic distillation with the aforementioned solvent. After the reaction was completed, the reaction solution was cooled to 100° C. From this reaction solution, the acid catalyst layer which settled to the bottom of the reactor was separated and removed.

The remaining reaction solution was further cooled to 30° C. and the cooled reaction solution and 15 g of sulfuric acid (purity not less than 98% weight) added thereto were stirred for 30 minutes. This treatment with sulfuric acid educed a resinous substance from the reaction solution. This resinous substance was separated from the reaction solution. Thereafter, the remaining reaction solution and 185 g of water added thereto were stirred for 15 minutes and then the water layer was separated.

Finally, the organic layer was distilled under a vacuum of 5 mmHg to expel the solvent. Consequently, there were obtained 118 g of yellow needle crystals of N-phenyl maleimide.

By high performance liquid chromatography, the crystals were found to have purity of 99.8% by weight, indicating the yeild thereof to be 70.4 mol% based on aniline.

CONTROL 3

The procedure of Example 30 was repeated, except that the treatment with sulfuric acid was omitted and the reaction solution freed from the acid catalyst layer was directly washed with water and distilled to expel the solvent. The N-phenyl maleimide consequently obtained was found to have purity of 91.2% by weight.

EXAMPLE 31

A flask provided with a thermometer, a condenser incorporating a water separator, a dropping funnel, and a stirrer was charged with 100 g of a petroleum fraction containing not less than 98% of an aromatic hydrocarbon having boiling points of 180° to 220° C. The petroleum fraction and 100 g of maleic anhydride added thereto were heated by elevating the internal temperature of the flask to 100° C. to dissolve the maleic anhydride in the petroleum fraction.

Then a solution of 100 g of cyclohexylamine in 600 g of the same solvent as described above was added dropwise while under stirring over a period of one hour to synthesize a slurry solution of N-cyclohexyl maleinamic acid in the aforementioned solvent.

Then, the aforementioned slurry solution and 60 g of ortho-phosphoric acid added thereto were heated and stirred at 210° C. for two hours to effect reaction, with the water formed by the reaction removed from the reaction system by azeotropic distillation with the solvent. After the reaction was completed, the reaction solution was heated at 200° C. to cause precipitation of an acid catalyst in the bottom. From the reaction solution, the acid catalyst layer was separated and removed.

Then, the remaining reaction solution was cooled to 60° C. and the cooled reaction solution and 100 g of water added thereto were stirred for 30 minutes. The water layer consequently formed was separated. This procedure of washing was repeated once more. The organic layer was distilled under a vacuum of 3 mmHg (abs) to expel the solvent.

Then, the residue of distillation in the flask and 0.3 g of copper dibutyl dithiocarbamate added thereto were distilled under a vacuum of 5 mmHg (abs) for 30 minutes, with the internal temperature of the flask kept at temperatures of 130° to 150° C. to isolate N-cyclohexyl maleimide. Consequently, there were obtained 137 g of bright white N-cyclohexyl maleimide crystals. The crystals were found to have purity of 99.8% by weight, indicating the yield thereof to be 75.7 mol% based on cyclohexylamine as the raw material.

EXAMPLE 32

A flask provided with a thermometer, a condenser incorporating a water separator, a dropping funnel, and a stirrer was charged with 100 g of ortho-xylene. The solvent and 100 g of maleic anhydride added thereto were heated by elevating the internal temperature of the flask to 70° C. to dissolve the maleic anhydride in the solvent.

Then, a solution of 90 g of aniline in 630 g of ortho-xylene was added thereto dropwise while under stirring over a period of 30 minutes to synthesize a slurry solution of N-phenyl maleinamic acid in ortho-xylene. During the course of this synthesis, the liquid temperature inside the flask was kept cooled to 70° C. to avoid the otherwise possible evolution of heat due to the dropwise addition of the solution of aniline in ortho-xylene.

Then, the aforementioned slurry solution and 20 g of ortho-phosphoric acid (85 wt.% aqueous solution), 0.06 g of zinc acetate, and 0.2 g of p-methoxyphenol added thereto were heated and stirred at 140° C. for three hours, with the water formed by the reaction removed from the reaction system by azeotropic distillation with ortho-xylene. After the reaction was completed, the reaction solution was cooled to 100° C. and the acid catalyst layer consequently separated from the reaction solution to the bottom was separated and removed.

Subsequently, the remaining reaction solution was further cooled to 30° C. and the cooled reaction solution and 15 g of sulfuric acid (purity of not less than 98 wt.%) added thereto were stirred for 30 minutes. This treatment with sulfuric acid induced eduction of a resinous substance from the reaction solution. This resinous substance was separated from the reaction solution. The remaining reaction solution and 185 g of water added thereto were stirred for 15 minutes to effect separation of a water layer.

Finally, the organic layer was distilled under a vacuum of 30 mmHg to expel ortho-xylene. Consequently, there were obtained 135 g of yellow needle crystals of N-phenyl maleimide.

By high performance liquid chromatography, the crystals were found to have purity of 99.5% by weight, indicating the yield thereof to be 80.3 mol% based on aniline.

CONTROL 4

The procedure of Example 32 was repeated, except that the treatment with sulfuric acid was omitted and the reaction solution freed from the acid catalyst layer was directly washed with water and distilled to expel orthoxylene. The N-phenyl maleimide consequently obtained was found to have purity of 90.0% by weight.

EXAMPLE 33

In a flask provided with a thermometer, a condenser incorporating a water separator, and a stirrer, 100 g of N-phenyl maleinamic acid and 400 g of ortho-xylene were stirred. Then, the resultant solution and 10 g of ortho-phosphoric acid (85 wt.% aqueous solution), 0.03 of zinc acetate, and 0.1 g of p-methoxyphenol added thereto were heated and stirred at 140° C. for three hours, with the water formed by the ensuing reaction removed by azeotropic distillation with ortho-xylene. After the reaction was completed, the resultant reaction solution was cooled to 120° to induce separation of a catalyst layer from the reaction solution to the bottom. The catalyst layer was removed.

Subsequently, the remaining reaction solution was further cooled to 80° C. and the cooled reaction solution and 10 g of sulfuric acid (purity of not less than 98 wt.%) added thereto were stirred for 20 minutes. This treatment with sulfuric acid induced separation of a resinous substance from the reaction solution. The resinous substance was separated from the reaction solution. The remaining reaction solution was cooled to 50° C. The cooled reaction solution and 200 g of water added thereto were stirred for 30 minutes. The water layer educed during the treatment was removed.

Finally, the organic layer was distilled under a vacuum of 30 mmHg of expel ortho-xylene. Consequently, there were obtained yellow needle crystals of N-phenyl maleimide.

By high performance liquid chromatography, the crystals were found to have purity of 99.6% by weight, indicating the yield thereof to be 81.1 mol% based on the N-phenyl maleinamic acid.

EXAMPLE 34

The procedure of Example 33 was repeated, except that the removal of the catalyst layer separated from the reaction solution to the bottom was omitted.

The N-phenyl maleimide consequently obtained was found to have purity of 99.5% by weight, indicating the yield thereof to be 80.5 mol%.

EXAMPLE 35

In a flask provided with the same devices as in Example 32, 100 g of ortho-xylene and 100 g of maleic anhydride were heated by elevating the internal temperature of the flask to 70° C. to dissolve maleic anhydride in the solvent.

Then, a solution of 124 g of o-chloroaniline in 870 g of ortho-xylene was added thereto dropwise while under stirring over a period of 30 minutes to synthesize a slurry solution of o-chlorophenyl maleinamic acid in ortho-xylene.

Then, the aforementioned slurry solution and 20 g ortho-phosphoric acid (85 wt.% aqueous solution), 0.07 g of zinc acetate, and 0.2 g of p-methoxyphenol added thereto were heated and stirred at 140° C. for three hours, with the water formed by the reaction removed from the reaction solution by azeotropic distillation with ortho-xylene. After the reaction was completed, the resultant reaction solution was cooled to 100° C. to induce separation of a catalyst layer from the reaction solution to the bottom. The catalyst layer was removed from the reaction solution.

Subsequently, the remaining reaction solution was further cooled reaction solution and 15 g of sulfuric acid (purity of not less than 98% by weight) added thereto were stirred for 30 minutes. By this treatment with sulfuric acid, a resinous substance was educed from the reaction solution. The resinous substance was removed from the reaction solution. The remaining reaction solution and 200 g of water added thereto were stirred at 30° C. for 15 minutes to induce separation of a water layer from the reaction solution.

The organic layer consequently obtained was distilled under a vacuum of 30 mmHg to expel ortho-xylene and obtain o-chlorophenyl maleimide.

By high performance liquid chromatography, this product was found to have purity of 99.7% by weight, indicating the yield thereof to be 80.1 mol% based on o-chloroaniline as the raw material.

EXAMPLE 36

In a flask provided with the same devices as in Example 32, 100 g of a solvent containing not less than 98% of a petroleum fraction of aromatic hydrocarbon having boiling points of 190° to 220° C. and 100 g of maleic anhydride were heated by elevating the internal temperature of the flask to 70° C. to dissolve maleic anhydride in the solvent.

Then, a solution of 124 g of o-chloroaniline in 870 g of the same solvent as mentioned above was added thereto dropwise while under stirring over a period of 30 minutes to synthesize a slurry solution of o-chlorophenyl maleinamic acid in ortho-xylene.

Then, the aforementioned slurry solution and 10 g of ortho-phosphoric acid (85 wt.% aqueous solution), 0.07 g of zinc acetate, and 0.5 g of tert-butyl catechol added thereto were heated and stirred at 185° C. for 1 hour, with the water formed by the reaction removed by azeotropic distillation with the solvent. After the reaction was completed, the resultant solution was cooled to 100° C. to induce separation of a catalyst layer from the reaction solution. The catalyst layer was removed from the reaction solution.

Subsequently, the remaining reaction solution was further cooled to 30° C. and the cooled reaction solution and 10 g of methane sulfonic acid added thereto were stirred for 30 minutes. By this treatment with methane sulfonic acid resinous substance was educed from the reaction solution. The resinous substance was removed from the reaction. The reaction solution and 200 g of water added thereto were stirred at 30° C. for 15 minutes to effect separation of the water phase.

The organic layer consequently obtained was distilled under a vacuum of 30 mmHg to product o-chlorophenyl maleimide.

The o-chlorophenyl maleimide was found by high performance liquid chromatography to have purity of 99.5% by weight, indicating the yield thereof to be 85.6 mol% based on o-chloroaniline as the raw material.

EXAMPLE 37

A glass flask having an inner volume of 10 liters was fitted with a thermometer, a stirrer, and a water separator. A solution of 530 g of maleic anhydride in 500 g of xylene was placed in the glass flask. Then, into the glass flask whose interior temperature was adjusted in advance to 130° C., a solution of 500 g of aniline in 4000 g of xylene was added gradually and piecemeal over a period of 30 minutes to synthesize a slurry solution of N-phenyl maleinamic acid in xylene.

The slurry solution so obtained and 200 g of ortho-phosphoric acid, 0.35 g of zinc acetate, and 1 g of copper dibutyl dithiocarbamate added thereto were heated at 140° C. for three hours. Then, the resultant reaction solution was cooled to 30° C., washed with 1000 g of water, and distilled under a vacuum to expel xylene. Consequently, there was obtained 830 g of yellow N-phenyl maleimide. It was found to contain 0.03% by weight of maleic acid, 0.20% by weight of maleinamic acid, and 5 ppm of phosphoric acid.

The crude N-phenyl maleimide and 1 g of copper dibutyl dithiocarbamate added thereto were heated and stirred by elevating the internal temperature of the flask to 160° C. The resultant reaction solution was distilled under a vacuum of 3 mmHg for two hours to produce 773 g of bright yellow N-phenyl maleimide crystals. The crystals were found to have purity of 99.7% by weight, indicating the yield thereof by distillation to be 98.0%.

CONTROL 5

The procedure of Example 37 was repeated, except that the washing treatment with water was omitted. Consequently, there were obtained 623 g of yellow crystals. These crystals were found to contain 1.0% by weight of maleic acid, 0.2% by weight of N-phenyl maleinamic acid, and 0.05% by weight of phosphoric acid. The yield by distillation was 78.1%.

CONTROL 6

The procedure of Example 37 was repeated, except that the washing treatment with water was omitted and the addition of the stabilizer in preparation for the distillation was omitted. Consequently, there were obtained yellow crystals. These crystals were found to have purity of 98.3% by weight. The yield by distillation was 60.0%. In this case, a resinous residue occurred in a large amount in the distillation kettle. Thus, the content of the kettle defied stirring.

EXAMPLE 38

In a vertical reaction tank measuring 600 cm in inside diameter and 800 cm in height and provided with a thermometer, a heating jacket, and a condenser incorporating a water separator, a mixed solution of 15 kg of maleic anhydride and 30 kg of xylene was placed, with the internal temperature of the reaction tank adjusted to 70° C.

Then, a mixed solution containing 13.5 kg of aniline and 70 kg of xylene was added thereto gradually and piecemeal over a period of 100 minutes. Consequently, there was obtained a slurry solution containing white crystals of N-phenyl maleinamic acid.

Subsequently, 3.2 kg of ortho-phosphoric acid, 9.6 g of zinc acetic acid, and 26.7 g of methoxy benzoquinone were added. By means of the heating jacket, the resultant reaction solution was heated to and kept at 136° C.

for six hours to effect reaction. Thereafter, the reaction solution was distilled under a vacuum of 30 mmHg (abs) to expel xylene. Consequently, there were obtained 24 kg of brown crystals of N-phenyl maleimide. The crystals were found to contain 0.1% by weight of N-phenyl maleinamic acid, 1.3% by weight of maleic acid, and 200 ppm of phosphoric acid.

The crystals were comminuted and washed twice with 50 kg of water at 30° C. The resultant washed powder was found to contain 0.005% by weight of N-phenyl maleinamic acid, 0.005% by weight of maleic acid, and not more than 1 ppm of phosphoric acid.

The N-phenyl maleimide consequently obtained and 25 g of copper dibutyl dithiocarbamate added thereto were heated and stirred by elevating the internal temperature of the reaction tank to 165° C. The resultant reaction solution was distilled under a vacuum of 3 mmHg (abs) for four hours. Consequently, there were obtained 21.5 kg of bright yellow N-phenyl maleimide crystals. The crystals were found to have purity of 99.5% by weight, indicating the yield thereof by distillation to be 98.2%.

EXAMPLE 39

In a flask provided with a thermometer, a condenser incorporating a moisture separator, a dropping funnel, and a stirrer, 100 g of p-cymene and 100 g of maleic anhydride added thereto were heated by elevating the internal temperature of the flask to 100° C. to dissolve the maleic anhydride.

Subsequently, a solution of 100 g of cyclohexylamine in 600 g of p-cymene was added thereto dropwise while under stirring to synthesize a slurry solution of N-cyclohexyl maleinamic acid in p-cymene.

Then, the slurry solution and 80 g of orthophosphoric acid, and 0.1 g of copper dibutyl dithiocarbamate added thereto were heated and stirred for seven hours, with the water formed by the reaction removed by azeotropic distillation with the solvent. After the reaction was completed, the reaction solution was held at 180° C. to induce separation of an acid catalyst from the reaction solution to the bottom. This catalyst layer was removed from the reaction solution.

Subsequently, the reaction solution was cooled to 60° C. and the cooled reaction solution and 100 g of water added thereto were stirred for 30 minutes to induce separation of a water layer. This washing treatment was repeated once more. The organic layer consequently obtained was distilled under a vacuum of 10 mmHg (abs) to expel the solvent.

Then, the reaction solution held in the flask and 0.3 g of copper dibutyl dithiocarbamate newly added thereto were held under a vacuum of 5 mmHg (abs) for 30 minutes with the internal temperature kept within the range of 130° to 150° C. to effect distillation of N-cyclohexyl maleimide. As the result, there were obtained 162 g of bright white N-cyclohexyl maleimide crystals. The crystals were found to have purity of 99.8% by weight, indicating the yield thereof to be 89.5 mol% based on cyclohexylamine as the raw material.

What is claimed is:

1. A method for the production of maleimides, which comprises subjecting maleinamic acids to ring-closure imidation in an aprotic non-polar organic organic solvent capable of forming an azeotrope with water in the presence of an acid catalyst and a metal-containing compound selected from the group consisting of oxides, acetates, maleates, succinates, nitrates, phosphates, chlorides, bromides, of zinc, chromium, cobalt, nickel, iron, aluminum iodides, and sulfates of zinc, chromium, cobalt, nickle, iron, aluminum, and palladium at a temperature in the range of 120° to 250° C. while removing the formed water in the form of an azeotrope with said organic solvent and thereafter purifying the produced crude maleimides.

2. A method according to claim 1, wherein said reaction temperature is in the range of 180° to 250° C.

3. A method according to claim 2, wherein said reaction temperature is in the range of 200° to 250° C.

4. A method according to claim 1, wherein said acid catalyst is used in an amount of 2 to 80 mol% to said maleinamic acids.

5. A method for the production of a maleimide which comprises subjecting a maleinamic acid to ring closure imidation in an aprotic non-polar organic solvent capable of forming an azeotrope with water in the presence of an acid catalyst consisting of at least one acid selected from the group consisting of sulfuric acid, sulfuric acid anhydride, p-toluene sulfonic acid, ortho-phosphoric acid, metaphosphoric acid and pyrophosphoric acid, and a metal-containing compound selected from the group consisting of oxides, acetates, maleates, succinates, nitrates, phosphates, chlorides, bromides, of zinc, chromium, cobalt, nickel, iron, aluminum and iodides, and sulfates of zinc, chromium, cobalt, nickel, iron, aluminum, and palladium at a temperature in the range of 120° C. to 250° C. while removing the formed water in the form of an azeotrope with said organic solvent and thereafter purifying the produced crude maleimide.

6. A method according to claim 1, wherein said metal-containing compound is a zinc containing compound.

7. A method according to claim 1, wherein said metal-containing compound is an acetic acid salt.

8. A method according to claim 1, wherein an amount of said metal-containing compound is 0.005 to 0.5 mol as the metal and an amount of said stabilizer is 0.005 to 0.5 mol per 100 mol of said maleinamic acids.

9. A method according to claim 1, wherein said purification comprises adding to said crude maleimides an organic acid or inorganic acid in an amount of at least 1% by weight based on the maleinamic acids used as the raw material, treating the resultant mixture at a temperature in the range of 5° to 100° C., and washing the resultant organic layer with the water thereby depriving the organic layer of water-soluble impurities.

10. A method according to claim 9, wherein said organic or inorganic acid is at least one acid selected from the group consisting of ortho-phosphoric acid, pyro-phosphoric acid, sulfuric acid, sulfuric acid anhydride, fuming sulfuric acid, methane sulfonic acid, chlorosulfonic acid, chloromaleic acid, para-toluene sulfonic acid and trifluoroacetic acid.

11. A method according to claim 10, wherein said acid is at least one acid selected from the group consisting of sulfonic acids, sulfuric acid, sulfuric acid anhydride and fuming sulfuric acid.

12. A method according to claim 9, wherein an amount of said acid is 1 to 30% by weight to said maleinamic acids.

13. A method according to claim 9, wherein said washing with water is carried out using 1 to 5 times of water to said starting maleinamic acids.

14. A method according to claim 1, wherein said purification comprises washing said crude maleimides with water and distilling the washed maleimides in the presence of a stabilizer, wherein said stabilizer is at least one member selected from the group consisting of quinones, phenols, thiodipropionoic acid esters, dithiocarbamates, salicylates, alkyldiphenylamines, phenothiazines, mercaptoimidazoles and triphenyl phosphates.

15. A method according to claim 14, wherein an amount of said stabilizer is not less than 10 ppm (by weight) to said crude maleimides.

16. A method according to claim 14, wherein the amount of said stabilizer is 100 to 2,000 ppm (by weight) to said crude maleimides.

17. A method according to claim 14, wherein said washing with water is carried out until an acid content in said crude maleimides decreases to not more than 0.5% by weight.

18. A method according to claim 14, wherein said stabilizer is dithiocarbamates.

19. A method according to claim 1, wherein said ring-closure imidation is carried out in the presence of a stabilizer, wherein said stabilizer is at least one member selected from the group consisting of quiinones, phenols, thiodipropionic acid esters, dithiocarbamates, salicylates, alkyldiphenylamines, phenothiazines, mercaptoimidazoles and triphenyl phosphates.

20. A method according to claim 19, wherein said stabilizer is at least one compound selected from the group consisting of quinones, phenols, thiodipropionic acid ester, dithiocarbamates, salicylates, alkyldiphenylamines, phenothiazines mercaptoimidazoles and triphenyl phosphates.

* * * * *